United States Patent [19]
Levinson et al.

[11] Patent Number: 5,823,952
[45] Date of Patent: Oct. 20, 1998

[54] PULSE OXIMETER SENSOR WITH DIFFERENTIAL SLIP COEFFICIENT

[75] Inventors: Mitchell Levinson, Pleasanton; Paul Mannheimer, Danville; Steven L. Nierlich; Phillip S. Palmer, both of San Leandro; Jessica Warring, Millbrae, all of Calif.

[73] Assignee: Nellcor Incorporated, Pleasanton, Calif.

[21] Appl. No.: 696,129

[22] Filed: Aug. 14, 1996

[51] Int. Cl.⁶ .................................................... A61B 5/00
[52] U.S. Cl. ...................... 600/338; 600/351; 600/376; 600/511
[58] Field of Search ..................................... 128/633, 634, 128/664, 665, 698; 600/338, 473, 476, 511, 351, 376

[56] References Cited

U.S. PATENT DOCUMENTS 4,928,691   5/1990   Nicholson et al. ...................... 128/633
5,099,842   3/1992   Mannheimer et al. .................. 128/633
5,377,673   1/1995   Van Dell et al. ........................ 128/698
5,507,752   4/1996   Elliot ....................................... 606/123

*Primary Examiner*—John P. Lacyk
*Assistant Examiner*—Eric F. Winakur
*Attorney, Agent, or Firm*—Townsend and Townsend and Crew LLP

[57] ABSTRACT

An improved fetal pulse oximeter sensor. The friction provided on the sensor head surface to engage the fetus is higher than the friction on the back side of the sensor head. Thus, any contact with a maternal surface by the back side of the sensor head is less likely to dislodge the sensor, since the maternal tissues will slide over the sensor head. The portion of the sensor surface in contact with the fetus' head will not move because of the increased friction. The increased friction can be achieved by using two different materials with different coefficients of friction, or by using a smooth surface on the back of the sensor head, and a rough surface on the sensor face.

14 Claims, 1 Drawing Sheet

PULSE OXIMETER SENSOR WITH DIFFERENTIAL SLIP COEFFICIENT

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

There are two basic types of fetal sensors, presenting part sensors and beyond the presenting part sensors. "Presenting part" refers to the region of the fetus that, during labor, resides external to the cervical os. "Beyond the presenting part" falls within the uterus and extends out to the cervical os. Sensors beyond the presenting part can typically use the uterine wall to bias the sensor against the fetus. For the presenting part, however, the fetus' scalp is typically exposed to the open birth canal, and such biasing is not as readily available, with positive attachment usually being used.

Presenting Part Sensors

Known techniques for presenting part sensors include invasive attachment to fetal tissue, such as by a screw attachment penetrating the tissue, or vacuum attachment mechanisms.

Examples of presenting part sensors include U.S. Pat. No. 3,827,428 which discloses a heartbeat sensor using a coil screw for attaching to the fetus' scalp. Pulse oximeter and other sensors which use such a spiral or screw-type arrangement are also shown in U.S. Pat. Nos. 4,281,659; 4,658,825; 5,154,175; 5,361,757; 5,411,024; and German Published Application No. DE4304691A1.

Examples of vacuum-type fetal sensors include that shown in U.S. Pat. No. 4,938,218 and PCT Published Application No. WO91/15996, which shows a bellows for providing a low-pressure vacuum source. U.S. Pat. No. 4,537,197 shows another vacuum attachment fetal sensor.

A number of other designs are also known. U.S. Pat. No. 4,299,232 shows a combination of a suction adhesion with a suction-cup type attachment, in conjunction with an electrical pole which pierces the fetus' skin. U.S. Pat. No. 5,024,226 requires a bore hole in the brain of the patient. U.S. Pat. No. 4,543,965 uses an inflatable membrane to bias the sensor against the fetus at the presenting part.

Non-Presenting Part Sensors

Other fetal sensors are designed to go beyond the presenting part. For instance, U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. WO91/07910 uses an inflatable sac to wedge the sensor against the fetus.

The intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

U.S. Pat. No. 5,099,842 shows a cluster of bumps over the emitter and/or detector of a pulse oximeter fetal sensor. These bumps are intended to provide a combing or scrubbing action to remove debris from the fetus' skin as the sensor is placed on the fetus so as to allow better light transmission into and out of the fetal tissue. These bumps are indicated as being over the emitter and detector, not the rest of the face of the sensor adjacent to the fetus.

SUMMARY OF THE INVENTION

The present invention provides an improved fetal pulse oximeter sensor which can be applied to the presenting part of a fetus or beyond the presenting part. The friction provided on the sensor head surface to engage the fetus is higher than the friction on the back side of the sensor head. Thus, any contact with a maternal surface, such as the cervix or uterine wall, by the back side of the sensor head, is less likely to dislodge the sensor, since the maternal tissues will slide over the sensor head. The portion of the sensor surface in contact with the fetus' head will not move because of the increased friction. The increased friction can be achieved by using two different materials with different coefficients of friction, or by using a smooth surface on the back of the sensor head, and a rough surface on the sensor face.

For a fuller understanding of the nature and advantages of the invention, reference should be made to the following description taken in conjunction with the accompanying drawings.

DESCRIPTION OF THE PREFERRED EMBODIMENT

Figure 1:
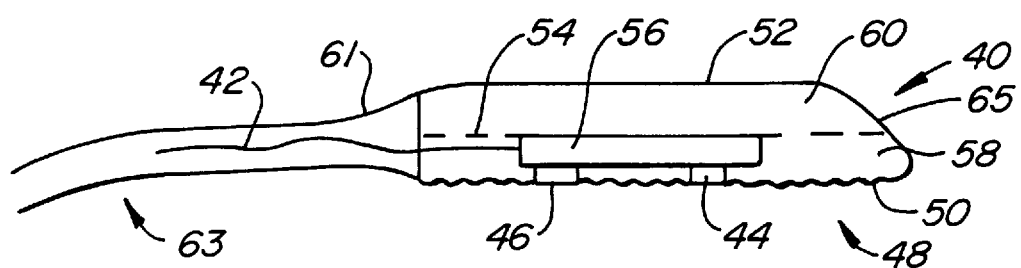
FIG. 1 is a side, sectional view of one embodiment of the invention showing the differential friction characteristics.

FIG. 1 shows an embodiment of the sensor head of the present invention. A sensor head 40 is attached to cable 42 and has an emitter 44 and a detector 46. As shown, a face 48 of the sensor has a rough surface 50, while a backside 52 of the sensor head is smooth. Rough surface 50 provides friction to keep the sensor head from slipping across the fetus' head. At the same time, a smooth surface 52 allows any part of the maternal tissues, such as the uterine wall or cervix, contacting the back of the sensor head to slide over it without dislodging the sensor from the fetus' head. The rough surface extends over at least 50% of the sensor face, and preferably over most of the sensor face. Additionally, the smooth surface preferably extends over 50%, and more preferably over more than 75% of the back side of the sensor.

Alternately, instead of using a rough surface 50, the sensor head could be manufactured of two different materials. A material providing sensor face 48 could have a higher coefficient of friction than a material providing backside 52.

In one embodiment, the two materials could be molded together, intersecting as indicated by a line 54. Emitter and detector 44 and 46 could be mounted on a carrier 56 placed in a mold of material 58, which is subsequently covered by a material 60. Alternately, the molding process could be reversed.

For example, one appropriate material for backside portion 60 would be polypropylene, while an appropriate material for front portion 58 would be santoprene.

As can be seen, the rough surface 50, or the material 58, extends across the entire face of the sensor around the emitter and detector. This is to be contrasted, for instance, with prior art U.S. Pat. No. 5,099,842, wherein bumps are provided over the emitter and detector only, and for a different purpose.

A fetal sensor according to one embodiment of the present invention does not have a firm means of attachment, and depends upon the friction of the sensor against the fetus' face induced by the pressing of the sensor by the uterine wall. When there is relative movement between the two (the fetus and the uterine wall) the differential friction will cause the sensor to stay attached to the fetus at the desired site, rather than moving with the uterine wall. This will reduce the number of required clinical adjustments.

Figure 2:
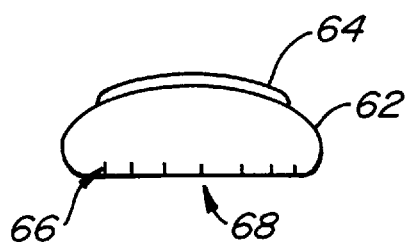
FIG. 2 is a front view of an alternate embodiment of the sensor of FIG. 1.

FIG. 2 illustrates an alternate embodiment of the sensor body showing a base material 62 for the body of the sensor, covered by a layer of slippery material 64. The base material 62 is molded first in a mold. The part is then moved to a larger mold, and a second, slippery material 64 is molded onto the base material. This gives a sensor with different materials on each side. Alternately, the slippery material could be molded first and inserted into a mold for the base material. In one embodiment, base material 62 is santoprene, while material 64 is a plastic, such polypropylene.

To increase the friction of the embodiment of FIG. 2, grooves or textured bumps 66 may be included in the face 68 of the base material 62. Alternately, any other uneven surface, such as small bumps or wells, could be used. In an alternate embodiment, a gritty material could be applied to the fetus engaging surface, such as a sandpaper-like material to provide increased friction. Alternately, a "fishscale"-like surface could be used so as to create a preferential slip direction. For example, the fishscales could extend toward the interior of the uterus to resist the sensor slipping farther into the uterus.

In addition, the sensor of FIG. 2 has a flat face 68 for engaging the fetus, thus encouraging more of the face to be in contact with the fetus and increasing the friction. By contrast, the back side with surface 64 is curved, such that only a small portion would be in contact with the maternal tissues at any time. The combination of a slippery surface and a curved surface allows the maternal tissues to slip over the back of the sensor without dislodging it from the fetus.

Preferably, the two materials used in making base material 62 and slippery material 64 are compatible such that they will adhere to each other during the molding process, and thus not delaminate subsequently. Alternately, an adhesive could be placed over base 62 and a separate molded slippery layer 64 could be attached. Or, in the manufacturing process, a rough surface or grooves could be left in the top of base material 62 in the region that will be covered by slippery material 64, to provide a better interconnection between the two molded portions.

Although FIG. 2 shows the slippery material 64 only on the top part of the sensor, in an alternate embodiment, slippery material 64 extends at least half-way around the curvature of the sides of base material 62 towards face 68. In an alternate embodiment, the slippery material may extend all the way down around the sides, since only the face will be in contact with the fetus and need the greater friction surface.

FIG. 1 also shows a cable 61 enclosing wires 42 attached to the sensor of FIG. 1. Cable 61 is preferably an overmolded plastic or other material which is substantially stiff and can be used to aid in inserting the sensor into the uterus. The substantially stiff cable provides support without the requirement of a separate insertion tool. Additionally, the cable 61 is preferably preformed to have a slight curvature 63 in order to bias the fetus engaging face against the fetus. Additionally, the sensor head has a bevelled, sloped face 65 to aid in insertion of the sensor body into the uterus. The slope extends from the fetus engaging surface 50 backwards towards the maternal engaging surface 52. This slope direction also reduces slippage by encouraging the maternal tissues to slide over the front surface while the surface 50 remains engaged with the fetus. A similar sloping surface may be used between cable 61 and the backside of the sensor, and the sides could be curved as well as shown in FIG. 2.

As will be understood by those of skill in the art, the present invention may be embodied in other specific forms without departing from the spirit or essential characteristics thereof. Accordingly, the above description is intended to be illustrative, but not limiting, of the scope of the invention which is set forth in the following claims.

What is claimed is:

1. A perinatal pulse oximeter sensor for application to a fetus for providing a signal corresponding to blood oxygen saturation, comprising:
    a sensor head having a non-adhesive fetus engaging surface for engagement with said fetus and a maternal engaging surface of said sensor head opposite said fetus engaging surface, at least 50% of said fetus engaging surface providing higher friction than said maternal engaging surface, allowing said sensor head to slip with respect to said maternal surface more easily than with respect to said fetus;
    a light emitter connected to said sensor head for emitting light of at least two wavelengths directed at said fetus; and
    a light detector mounted in said sensor head for collecting light to be detected and generating said signal.

2. The sensor of claim 1 wherein
    said 50% of said fetus engaging surface comprises a textured surface.

3. The sensor of claim 1 wherein said 50% of said fetus engaging surface comprises a first material having a higher coefficient of friction than a second material on said maternal engaging surface.

4. The sensor of claim 1 wherein said fetus engaging surface is substantially flat, and said maternal engaging surface is curved.

5. A perinatal pulse oximeter sensor for application to a fetus for providing a signal corresponding to blood oxygen saturation, comprising:
    a sensor head having a fetus engaging surface for engagement with said fetus and a maternal engaging surface of said sensor head opposite said fetus engaging surface, said sensor head including slip means on a body of said sensor for allowing said sensor head to slit with respect to said maternal surface more easily than with respect to said fetus;
    a light emitter connected to said sensor head for emitting light of at least two wavelengths directed at said fetus;
    a light detector mounted in said sensor head for collecting light to be detected and generating said signal; and
    a substantially stiff cable attached to said sensor head, said cable being preformed to bias said fetus engaging surface against said fetus.

6. A perinatal sensor for application to a fetus, comprising:
    a sensor body having a non-adhesive fetus engaging surface for engagement with said fetus and a maternal engaging surface of said sensor head opposite said fetus engaging surface, at least 50% of said fetus engaging surface being a higher friction surface than said maternal engaging surface; and
    a sensor mounted in said sensor body.

7. The sensor of claim 7 wherein said 50% of said fetus engaging surface is
    a textured surface and said maternal engaging surface is a smooth surface.

8. The sensor of claim 6 wherein said 50% of said fetus engaging surface has a higher coefficient of friction than a material on said maternal engaging surface.

9. The sensor of claim 6 wherein said fetus engaging surface is substantially flat, and said maternal engaging surface is curved.

10. A perinatal sensor for application to a fetus, comprising:
    a sensor body having a fetus engaging surface for engagement with said fetus and a maternal engaging surface of said sensor head opposite said fetus engaging surface, said fetus engaging surface being a higher friction surface than said maternal engaging surface;
    a sensor mounted in said sensor body; and
    a substantially stiff cable attached to said sensor body, said cable being preformed to bias said fetus engaging surface against said fetus.

11. A perinatal sensor for application to a fetus, comprising:
    a sensor body having a non-adhesive fetus engaging surface for engagement with said fetus and a maternal engaging surface of said sensor head opposite said fetus engaging surface, a first material on said fetus engaging surface having a higher coefficient of friction than a second material on said maternal engaging surface, said second material covering at least 50 percent of said maternal engaging surface;
    wherein said fetus engaging surface is substantially flat, and said maternal engaging surface is curved;
    a light emitter connected to said sensor body for emitting light of at least two wavelengths directed at said fetus; and
    a light detector mounted in said sensor body for collecting light to be detected.

12. A perinatal sensor for application to a fetus, comprising:
    a sensor body having a fetus engaging surface for engagement with said fetus and a maternal engaging surface of said sensor head opposite said fetus engaging surface, a first material on said fetus engaging surface having a higher coefficient of friction than a second material on said maternal engaging surface, said second material covering at least 50 percent of said maternal engaging surface;
    wherein said fetus engaging surface is substantially flat, and said maternal engaging surface is curved;
    a light emitter connected to said sensor body for emitting light of at least two wavelengths directed at said fetus;
    a light detector mounted in said sensor body for collecting light to be detected; and
    a textured surface on at least 50 percent of said fetus engaging surface, and a smoother surface on said maternal engaging surface.

13. A perinatal sensor for application to a fetus, comprising:
    a sensor body having a fetus engaging surface for engagement with said fetus and a maternal engaging surface of said sensor head opposite said fetus engaging surface, a first material on said fetus engaging surface having a higher coefficient of friction than a second material on said maternal engaging surface, said second material covering at least 50 percent of said maternal engaging surface;
    wherein said fetus engaging surface is substantially flat, and said maternal engaging surface is curved;

a light emitter connected to said sensor body for emitting light of at least two wavelengths directed at said fetus;

a light detector mounted in said sensor body for collecting light to be detected; and a substantially stiff cable attached to said sensor body, said cable being preformed to bias said fetus engaging surface against said fetus.

14. A method for applying a perinatal sensor to a fetus, comprising the steps of:

providing a sensor body having a non-adhesive fetus engaging surface for engagement with said fetus and a maternal engaging surface of said sensor head opposite said fetus engaging surface, at least 50% of said fetus engaging surface being a higher friction surface than said maternal engaging surface;

inserting said sensor body between a fetus and a uterine wall; and allowing movement of said uterine wall over said maternal engaging surface while said fetus engaging surface remains in contact with said fetus.

* * * * *

UNITED STATES PATENT AND TRADEMARK OFFICE
CERTIFICATE OF CORRECTION

PATENT NO. : 5,823,952
DATED : October 20, 1998
INVENTOR(S) : Mitchell Levinson et al.

It is certified that error appears in the above-identified patent and that said Letters Patent is hereby corrected as shown below:

ON THE TITLE PAGE

Item [73] Assignee: Nellcor Puritan Bennett Incorporated.

Col. 5, on line 44 "slip" should be --slip--.

Signed and Sealed this

Twenty-third Day of March, 1999

Attest:

Q. TODD DICKINSON

*Attesting Officer*  *Acting Commissioner of Patents and Trademarks*